(12) United States Patent
Ehlers et al.

(10) Patent No.: US 11,781,591 B2
(45) Date of Patent: Oct. 10, 2023

(54) RADIAL VENTILATOR

(71) Applicant: ebm-papst St. Georgen GmbH & Co. KG, St. Georgen (DE)

(72) Inventors: Volker Ehlers, St. Georgen (DE); Katrin Schaake, Ueberlingen (DE)

(73) Assignee: ebm-papst St. Georgen GmbH & Co. KG, St. Georgen (DE)

( * ) Notice: Subject to any disclaimer, the term of this patent is extended or adjusted under 35 U.S.C. 154(b) by 232 days.

(21) Appl. No.: 17/287,074

(22) PCT Filed: May 14, 2019

(86) PCT No.: PCT/EP2019/062393
§ 371 (c)(1),
(2) Date: Apr. 20, 2021

(87) PCT Pub. No.: WO2020/104075
PCT Pub. Date: May 28, 2020

(65) Prior Publication Data
US 2021/0355946 A1    Nov. 18, 2021

(30) Foreign Application Priority Data

Nov. 23, 2018   (DE) .................... 10 2018 129 608.8
Nov. 23, 2018   (DE) .................... 10 2018 129 611.8
Nov. 23, 2018   (DE) .................... 10 2018 129 613.4

(51) Int. Cl.
F04D 29/08    (2006.01)
F04D 17/08    (2006.01)
(Continued)

(52) U.S. Cl.
CPC ......... *F04D 29/083* (2013.01); *A61M 16/006* (2014.02); *F04D 1/00* (2013.01);
(Continued)

(58) Field of Classification Search
CPC ............. A61M 16/0066; A61M 16/006; F04D 25/0606; F04D 17/16; F04D 29/4226;
(Continued)

(56) References Cited

U.S. PATENT DOCUMENTS

| 8,973,576 B2 * | 3/2015 | Kenyon | ............... F04D 29/4233 |
| | | | 128/204.19 |
| 2014/0069432 A1 * | 3/2014 | Mebasser | ............ F04D 25/0613 |
| | | | 128/205.25 |
| 2018/0274545 A1 * | 9/2018 | Ragg | ..................... F04D 29/083 |

FOREIGN PATENT DOCUMENTS

| DE | 102 45 798 A1 | 4/2004 |
| DE | 11 2014 002022 T5 | 12/2015 |

(Continued)

OTHER PUBLICATIONS

Notification of First Office Action and Search Report dated Jul. 7, 2022, which issued in the corresponding Chinese Patent Application 201980067766.2.

(Continued)

*Primary Examiner* — Peter J Bertheaud
(74) *Attorney, Agent, or Firm* — Dickinson Wright PLLC

(57) ABSTRACT

A radial fan (1) is provided with a motor (2) and a fan housing, an outer part (4) and an inner part (5) that form a spiral-like pressure chamber (D). A pressure connector (33) which forms an outlet (44) of the radial fan (1) is arranged on the outer part. The fan housing is equipped with a fan wheel (3) which is arranged on a shaft (7) connected to the motor (2), wherein an annular flow divider (8) which surrounds the fan wheel (3) is arranged adjacently to the fan wheel (3) in a radial direction. The flow divider together with the fan housing forming a diffuser (9), which transitions directly into the pressure chamber (D), about the fan wheel (3).

18 Claims, 3 Drawing Sheets

(51) Int. Cl.
*F04D 29/059* (2006.01)
*F04D 1/00* (2006.01)
*F04D 13/06* (2006.01)
*F04D 25/06* (2006.01)
*F04D 29/42* (2006.01)
*F04D 29/44* (2006.01)
*F04D 29/056* (2006.01)
*A61M 16/00* (2006.01)
*F04D 17/16* (2006.01)
*F04D 29/28* (2006.01)
*F04D 29/16* (2006.01)
*F16C 19/54* (2006.01)
*F16C 25/08* (2006.01)

(52) U.S. Cl.
CPC ............. *F04D 13/06* (2013.01); *F04D 17/08* (2013.01); *F04D 17/16* (2013.01); *F04D 25/062* (2013.01); *F04D 25/0606* (2013.01); *F04D 29/056* (2013.01); *F04D 29/059* (2013.01); *F04D 29/162* (2013.01); *F04D 29/281* (2013.01); *F04D 29/4226* (2013.01); *F04D 29/4233* (2013.01); *F04D 29/441* (2013.01); *F16C 19/548* (2013.01); *F16C 25/083* (2013.01); *F16C 2360/46* (2013.01)

(58) Field of Classification Search
CPC .. F04D 29/441; F04D 29/4233; F04D 29/281; F04D 25/062; F04D 29/056; F04D 29/059; F04D 29/162; F04D 29/083; F04D 1/00; F04D 13/06; F04D 17/08
See application file for complete search history.

(56) References Cited

FOREIGN PATENT DOCUMENTS

DE 202018106694 U1 11/2018
WO 2016169610 A1 10/2016

OTHER PUBLICATIONS

International Search Report and Written Opinion in German, dated Jul. 30, 2019, issued in the corresponding PCT Patent Application No. PCT/EP2019/062393, including English Translation of ISR.

* cited by examiner

RADIAL VENTILATOR

FIELD

The disclosure relates to a radial fan formed as a high-speed radial fan with improved pressure buildup and efficiency with simultaneously low noise development.

BACKGROUND

Type-defining radial fans are known from the prior art, for example from German utility model DE202018106694U1.

Corresponding radial fans essentially have the problem of small installation space; however, the flow should be conveyed as optimally as possible from intake to outlet. Good flow conditions improve the efficiency, the pressure buildup, and the acoustics of the radial fan. Typically, radial fans have a spiral-like housing, which absorbs, decelerates, and finally converts the rapid flow discharged by the radial impeller into usable pressure. In this case, shock-free deceleration is advantageous for the pressure buildup.

SUMMARY

The object of the disclosure is to provide a radial fan, the flow of which is improved, in order to have the highest level of efficiency possible with simultaneously improved acoustics. The necessary installation space of the radial fan in this case should be as small as possible.

This object is achieved by the combination of features according to claim 1.

According to example embodiments, a radial fan having a motor and a fan housing is proposed, which forms a spiral-like pressure chamber with an outer part and an inner part. A pressure connector, which forms an outlet of the radial fan, is arranged on the outer part. A fan wheel arranged on a shaft connected to the motor is provided in the fan housing, which fan wheel intakes air axially and discharges air radially during operation. An annular flow divider surrounding the fan wheel is arranged adjacently to the fan wheel in a radial direction, which flow divider together with the fan housing forms a diffuser about the fan wheel, which diffuser transitions directly into the pressure chamber.

It is important for the fan wheel that it has even counterpressure over the entire circumference at the outlet. Thus, each blade of the fan wheel optimally contributes to the flow. A nonuniform pressure distribution around the fan wheel would lead to negative and undesired stalls and backflows into the fan wheel. For the advantageous pressure buildup from the fan wheel into the pressure chamber, the flow divider is provided about the fan wheel, which flow divider together with the fan housing provides a diffuser for the flow exiting from the fan wheel, which diffuser has a direct fluid connection with the pressure chamber and provides the uniform counter-pressure for the fan wheel. The radially discharged air flows through the diffuser going from radially inward to radially outward up to the radial end thereof and then enters the pressure chamber.

The entry into the pressure chamber is naturally radially adjacent the diffuser; however, the spiral-like pressure chamber itself is preferably formed axially adjacent the diffuser in an adjacent axial plane such that the flow flows from the flow divider into the pressure chamber tangentially. The flow divider can extend far radially outward such that the inflow occurs in the outer radial region of the fan housing and the spiral-like pressure chamber thereof and, in doing so, generates a defined corkscrew vortex. Losses due to turbulence in the spiral-like pressure chamber can thereby be prevented.

One advantageous embodiment of the radial fan provides that the outer part has a constant outer diameter adjacent the pressure chamber, and a spiral shape of the pressure chamber is determined exclusively by the inner part. The installation space of the radial fan is especially compact in this embodiment. By using the flow divider, the disadvantages resulting from the spirals of the pressure chamber generated via the inner part can be compensated for.

Furthermore, a design of the radial fan is preferred in which the spiral-like pressure chamber is formed by an axial and radial extension. The spiral shape can be realized with comparatively small space requirements due to the enlargement of the pressure chamber in two directions.

The flow divider with the radial fan preferably protrudes opposite a radial inner wall surface of the inner part in the radial direction and thus forms an axial surface of the pressure chamber. The spiral-like pressure chamber is axially adjacent the diffuser, in which the flow divider advantageously forms a flow surface for the diffuser on a first axial side and an axial wall surface for the spiral-like pressure chamber on an opposite axial surface.

In one design variant of the radial fan, it is provided that the motor has a circuit board with electronic components, and the inner part separates the pressure chamber as relates to the circuit board. This results in an axially nested, compact arrangement of the pressure chamber and motor electronics.

Furthermore, a design of the radial fan is favorable in which the inner part is an integral component of the rotor of the motor. The number of parts and the installation space required for this are minimized.

In particular, the motor is formed as a canned motor with an axially open bearing tube. In this case, it is advantageous to form the bearing tube and the inner part as a single piece. Thus, motor functions can be combined with those of the aerodynamics for flow control without further parts being required.

In one refinement, the radial fan is further characterized in that the flow divider is an integral component of the bearing tube and the rotor assembly. In one favorable embodiment, the flow divider is inserted into the axially open bearing and takes on the shape of the inner part, at least in sections.

In one embodiment, the flow divider has a pot-like axial depression with a diameter which substantially corresponds to an outer diameter of the fan wheel. The fan wheel is inserted into the depression, axially in sections, with the smallest possible dimension of 0.2-0.5 mm in order to ensure the rotation such that the flow discharged by the fan wheel is directly influenced by the radially adjacent section of the flow divider, which forms the diffuser. The depression enables an axially compact construction of the fan wheel and flow divider.

In one refinement, the radial fan is characterized in that the flow divider has a curvature, at least in sections, on its free end as relates to the pressure chamber. In particular, the curvature is provided on a radial end of the diffuser in order to improve the tangential inflow into the pressure chamber.

As a further design variant of the radial fan, the inner part has a circumferential axial protrusion, which adjoins the outer part, on its radial outer edge section. This results in an axial depression in the inner part in the pressure chamber, in which simultaneously a sufficient contact surface is ensured between the inner part and the outer part via the circumferential protrusion.

Furthermore, in one design variant, the radial fan comprises at least one bearing for supporting the shaft, which bearing is arranged between the flow divider and the shaft. Preferably, two bearings spaced apart axially are provided which are tensioned via a spring and each of which is arranged between the flow divider and the shaft.

In this radial fan, the motor is preferably accommodated in a housing cover. The outer part, the inner part, and the housing cover are sealed off to one another with seals in order to minimize pressure losses.

BRIEF DESCRIPTION OF THE DRAWINGS

Other advantageous further embodiments of the disclosure are characterized in the dependent claims and/or are shown in more detail in the following by means of the figures, along with the description of the preferred embodiment of the disclosure.

DETAILED DESCRIPTION OF EXAMPLE EMBODIMENTS

Figure 1:
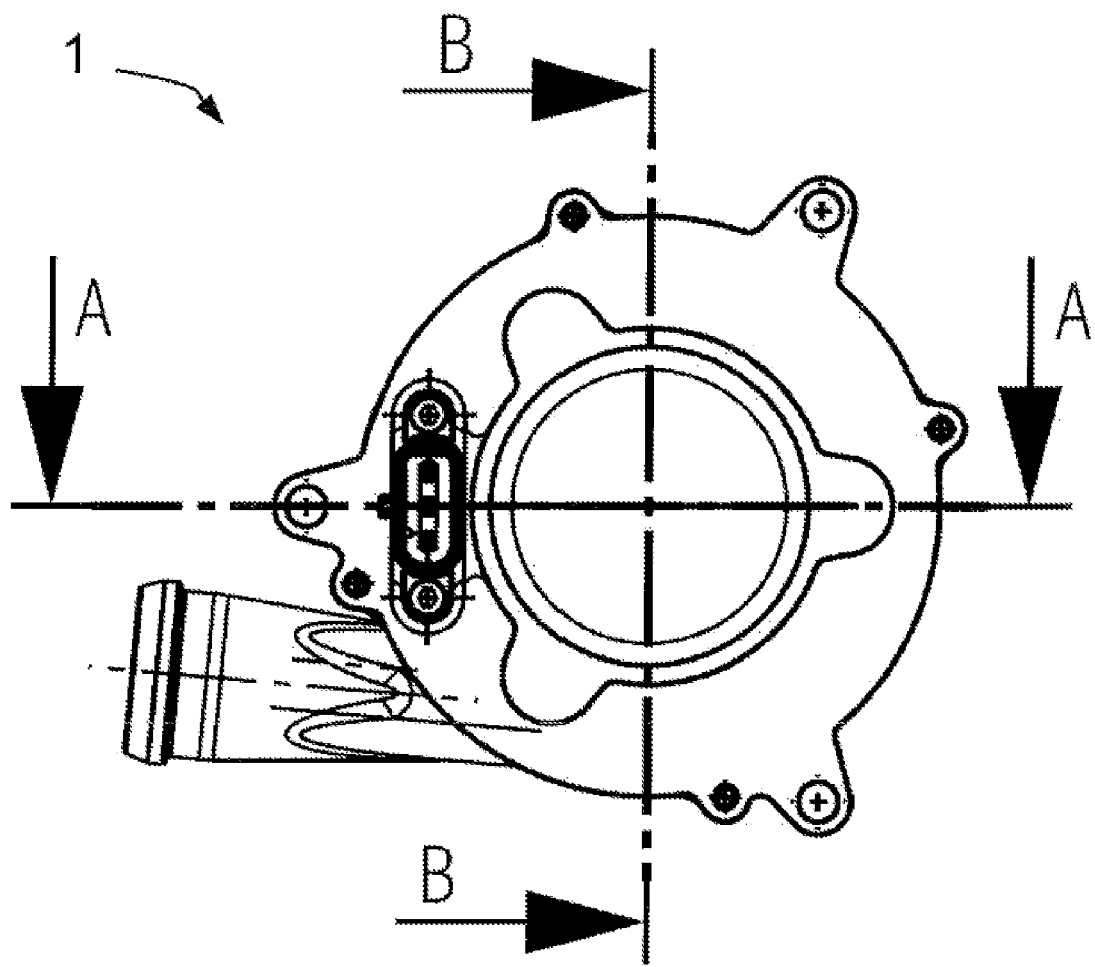
FIG. 1 is a top view of a radial fan.
Figure 2:
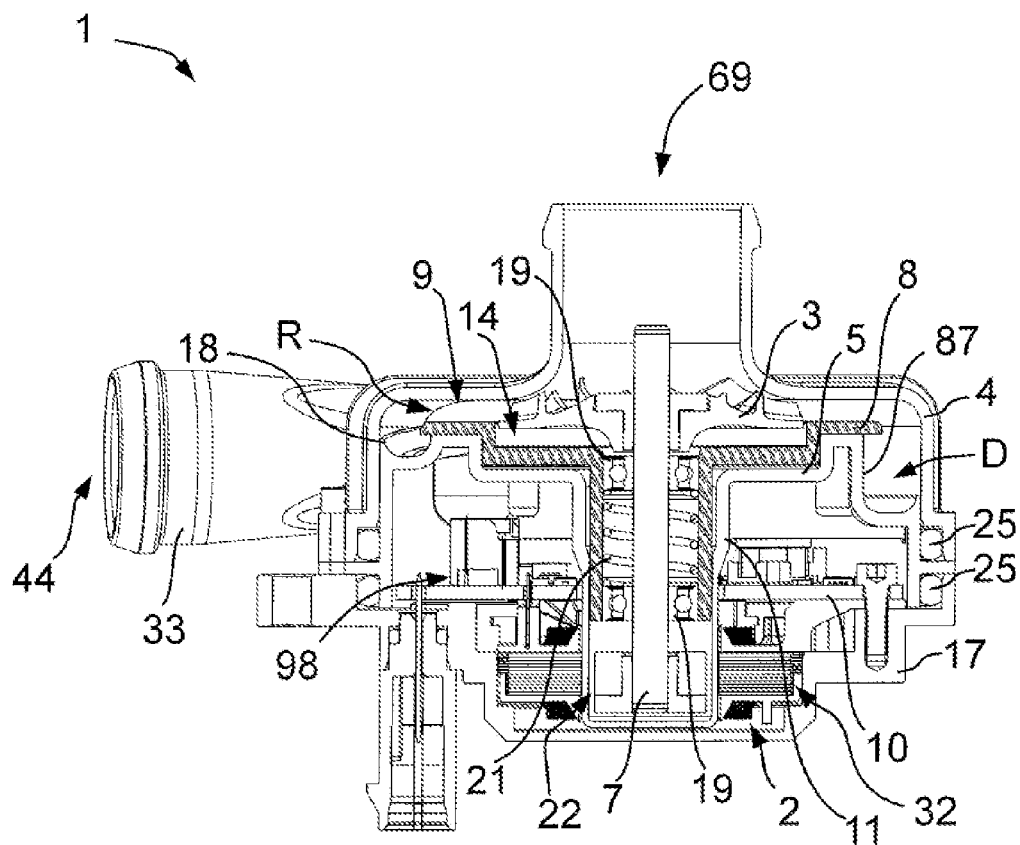
FIG. 2 is a sectional view A-A from FIG. 1.
Figure 3:
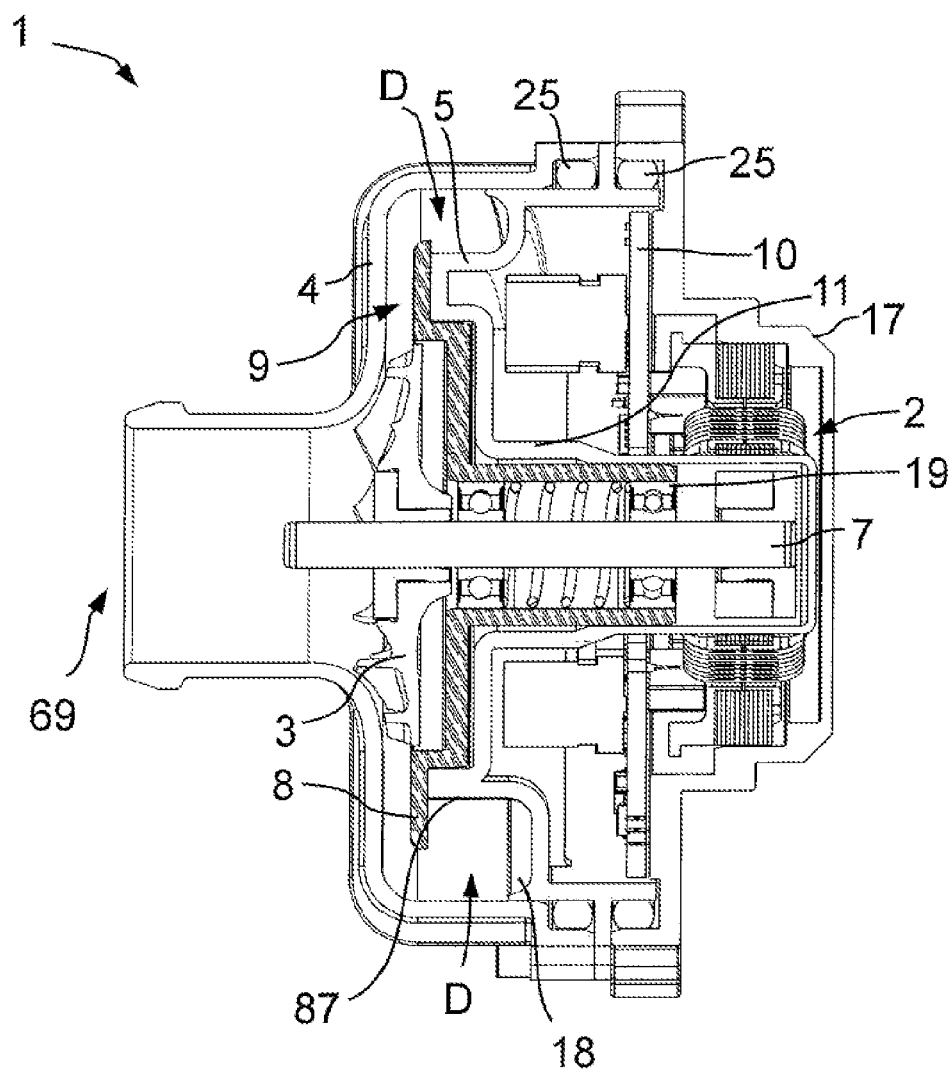
FIG. 3 is a sectional view B-B from FIG. 1.

FIGS. 1-3 show an exemplary embodiment of a radial fan 1 according to the disclosure in an axial top view and two sectional views A-A and B-B.

The radial fan 1 comprises an electric motor 2 formed as a canned motor with a rotor 22 and a stator 32. The magnets of the rotor 22 are attached to the shaft 7, which extends along the axis of rotation axially through the radial fan 1. The fan wheel 3 formed as a radial fan wheel is attached to the shaft 7, which fan wheel intakes air axially via its impeller blades by means of the inlet 69 and discharges it at the outlet 44 via the pressure connector 33. Furthermore, the radial fan 1 comprises the fan housing, which is formed by the outer part 4, the inner part 5, and the housing cover 17, in which the motor 2 is accommodated. The circuit board 10 with the electronic components 98 affixed thereto is attached to the housing cover 17 axially between the inner part 5 and the motor 2 for controlling the radial fan 1. On the one hand, the inner part 5 forms a free space for the electronic components 98 on a side pointing toward the motor 2; on the other hand, it determines, with the outer part, the spiral-like pressure chamber D on the opposite, axial side of the radial fan 1 pointing toward the outer part 4. In this case, the inner part 5 extends radially outward to between the outer part 4 and the housing cover 17 and is fixed in position via the outer part 4 and the housing cover 17. Seals 25 are provided in order to seal off the two axial regions separated by the inner part 5. The electronic components 98 are arranged in the free space adjacent the pressure chamber D and consequently facing the flow, whereby a discharge of heat takes place to the inner part 5 and thus cooling occurs.

The annular flow divider 8 surrounding the fan wheel 3 is arranged radially adjacent the fan wheel 3, which flow divider, together with the inner wall surface of the outer part 4 of the fan housing, forms the diffuser 9 about the fan wheel 3. The inner wall surface of the outer part 4 and the flow divider 8 extend radially outward in the region of the diffuser 9, perpendicular to the axis of rotation. In one alternative embodiment, the wall surfaces, which point toward one another, of the flow divider and of the outer part also converge. The free end of the flow divider 8 forms the end of the diffuser 9 and has a curvature R. The diffuser 9 transitions directly into the pressure chamber D. The spiral shape of the pressure chamber D is formed exclusively via the inner part 5; the outer part 4 in this case has a constant diameter. With reference to FIGS. 2 and 3, it can be easily seen that the pressure chamber D extends axially and also radially due to the shaping of the inner part 5. The flow divider 8 protrudes in the radial direction as relates to the radial inner wall surface 87 of the inner part 5 and partially forms an upper axial surface of the pressure chamber D. In one alternative embodiment, the flow divider terminates circumferentially, partially is flush, with the inner wall surface. At the bottom, the inner part 5 has a circumferential channel-shaped recess, which transitions radially on the outside into the axial protrusion 18, which forms a contact surface as relates to the inner wall surface of the outer part 4. The pressure chamber D is offset axially, but is formed directly adjacent the diffuser 9 such that the flow generated by the fan wheel 3 flows tangentially from the diffuser 9 into the pressure chamber D. The pressure connector 33 is formed on the outer part 4, as an extension of the pressure chamber D.

The bearing tube 11 extends through the circuit board 10 axially centrally and accommodates the rotor 22. The bearing tube 11 is formed by the inner part 5 as a single piece. The flow divider 8 is formed as an insert and inserted into the bearing tube 11. Thus, it forms an integral component of the bearing tube 11 and consequently the rotor assembly. The shaft 7 is supported on the flow divider 8 and the bearing tube 11 via two bearings 19. The two bearings 19 are tensioned in the axial direction via the springs 21. Alternatively, the support of the shaft 7 can also take place opposite the bearing tube 11.

On the side of the fan wheel 3, the flow divider 8 has a pot-like axial depression 14, into which the fan wheel 3 with its base plate is inserted such that the exit of the fan wheel 3 and the surface of the adjoining flow divider 8 are flush in an axial plane. The diameter of the depression 14 is equal to the outer diameter of the base plate of the fan wheel 3 such that there is a substantially gap-free transition from the fan wheel 3 to the flow divider 8. Substantially gap-free in this case means that the rotation of the fan wheel 3 opposite the flow divider 8 is ensured.

The invention claimed is:

1. A radial fan (1) with a motor (2) and a fan housing, an outer part (4) and an inner part (5) of which form a spiral-like pressure chamber (D), wherein a pressure connector (33) which forms an outlet (44) of the radial fan (1) is arranged on the outer part, wherein the fan housing is equipped with a fan wheel (3) which is arranged on a shaft (7) connected to the motor (2), and wherein an annular flow divider (8) which surrounds the fan wheel (3) is arranged adjacently to the fan wheel (3) in a radial direction, wherein the flow divider (8), together with the fan housing, forms a diffuser (9), which transitions directly into the pressure chamber (D), about the fan wheel (3), wherein the flow divider (8) has a pot-like axial depression (14), which has a diameter which substantially corresponds to an outer diameter of the fan wheel (3), wherein the fan wheel (3) is inserted into the depression (14) axially in sections.

2. The radial fan according to claim 1, characterized in that the outer part has a constant outer diameter adjacent the pressure chamber (D), and a spiral shape of the pressure chamber (D) is determined exclusively by the inner part (5).

3. The radial fan according to claim 1, characterized in that the spiral-like pressure chamber (D) is formed by an axial and radial extension.

4. The radial fan according to claim 1, characterized in that the flow divider (8) protrudes, at least in sections, opposite a radial inner wall surface of the inner part (5) in the radial direction and thus forms an axial surface of the pressure chamber (D).

5. The radial fan according to claim 1, characterized in that the motor (2) has a circuit board (10) with electronic components and the inner part (5) separates the pressure chamber (D) as relates to the circuit board (10).

6. The radial fan according to claim 1, characterized in that the motor (2) is formed as a canned motor with a bearing tube (11) which is open axially on at least one side.

7. The radial fan according to claim 6, characterized in that the bearing tube (11) and the inner part (5) are formed as a single piece.

8. The radial fan according to claim 6, characterized in that the flow divider (8) is an integral component of the bearing tube (11).

9. The radial fan according to claim 1, further comprising at least one bearing (19) for supporting the shaft (7), wherein the at least one bearing (19) is arranged between the flow divider (8) and the shaft (7).

10. The radial fan according to claim 1, characterized in that the flow divider (8) has a curvature (R), at least in sections, on its free end as relates to the pressure chamber (D).

11. The radial fan according to claim 1, characterized in that the inner part (5) has a circumferential axial protrusion (18), which adjoins the outer part (4), on its radial outer edge section.

12. The radial fan according to claim 1, characterized in that the motor (2) is accommodated in a housing cover (17), wherein the outer part (4), the inner part (5), and the housing cover (17) are sealed off from one another using seals (25).

13. A radial fan (1) with a motor (2) and a fan housing, an outer part (4) and an inner part (5) of which form a spiral-like pressure chamber (D), wherein a pressure connector (33) which forms an outlet (44) of the radial fan (1) is arranged on the outer part, wherein the fan housing is equipped with a fan wheel (3) which is arranged on a shaft (7) connected to the motor (2), and wherein an annular flow divider (8) which surrounds the fan wheel (3) is arranged adjacently to the fan wheel (3) in a radial direction, wherein the flow divider (8), together with the fan housing, forms a diffuser (9), which transitions directly into the pressure chamber (D), about the fan wheel (3), characterized in that the motor (2) is formed as a canned motor with a bearing tube (11) which is open axially on at least one side, and the flow divider (8) is inserted into the axially open bearing tube (11).

14. The radial fan according to claim 13, characterized in that the bearing tube (11) and the inner part (5) are formed as a single piece.

15. The radial fan according to claim 13, characterized in that the flow divider (8) is an integral component of the bearing tube (11).

16. The radial fan according to claim 13, characterized in that the outer part has a constant outer diameter adjacent the pressure chamber (D), and a spiral shape of the pressure chamber (D) is determined exclusively by the inner part (5).

17. The radial fan according to claim 13, characterized in that the spiral-like pressure chamber (D) is formed by an axial and radial extension.

18. The radial fan according to claim 13, characterized in that the flow divider (8) protrudes, at least in sections, opposite a radial inner wall surface of the inner part (5) in the radial direction and thus forms an axial surface of the pressure chamber (D).

* * * * *